United States Patent
Lundquist

(10) Patent No.: US 8,721,603 B2
(45) Date of Patent: May 13, 2014

(54) SYRINGE WITH CO-MOLDED HUB AND CANNULA

(75) Inventor: Jon Tyler Lundquist, Chandler, AZ (US)

(73) Assignee: West Pharmaceutical Services, Inc., Exton, PA (US)

( * ) Notice: Subject to any disclaimer, the term of this patent is extended or adjusted under 35 U.S.C. 154(b) by 223 days.

(21) Appl. No.: 13/237,429

(22) Filed: Sep. 20, 2011

(65) Prior Publication Data

US 2012/0010573 A1 Jan. 12, 2012

Related U.S. Application Data

(63) Continuation-in-part of application No. 12/680,609, filed as application No. PCT/US2009/031112 on Jan. 15, 2009, now Pat. No. 8,496,862.

(60) Provisional application No. 61/021,186, filed on Jan. 15, 2008.

(51) Int. Cl.
*A61M 5/00* (2006.01)
*A61M 5/32* (2006.01)
*A61M 5/178* (2006.01)

(52) U.S. Cl.
USPC ...... 604/240; 604/164.07; 604/181; 604/187; 604/272

(58) Field of Classification Search
USPC ............ 604/181, 187, 164.07, 272, 240, 604/190–199, 241–249, 263
See application file for complete search history.

(56) References Cited

U.S. PATENT DOCUMENTS

| 2,998,050 A | 8/1961 | Hamilton et al. |
| 3,093,134 A | 6/1963 | Roehr |

(Continued)

FOREIGN PATENT DOCUMENTS

| CH | 657990 A5 | 10/1986 |
| CN | 1498123 A | 5/2004 |

(Continued)

OTHER PUBLICATIONS

International Preliminary Report on Patentability Issued Jul. 20, 2010 in Int'l Application No. PCT/US2009/031112; Written Opinion.

(Continued)

*Primary Examiner* — Emily Schmidt
*Assistant Examiner* — Lauren M Peng
(74) *Attorney, Agent, or Firm* — Panitch Schwarze Belisario & Nadel LLP

(57) ABSTRACT

A prefilled syringe for injecting medicament into a patient includes a barrel constructed of a polymeric material, a cannula and a hub. The barrel has a diameter, a longitudinal axis, a proximal end and a distal end. The cannula has a proximal end and a tip opposite the proximal end. The proximal end of the cannula is fixed to the distal end of the barrel. The cannula is positioned generally coaxially with the longitudinal axis. The hub is integrally formed with the distal end. The hub includes a rib section and a cap. The rib section has a generally cruciform cross-section taken along a rib plane. The rib plane is generally perpendicular to the longitudinal axis. The cap has a generally U-shaped cross-section taken along a longitudinal plane. The longitudinal plane is generally parallel to the longitudinal axis.

9 Claims, 13 Drawing Sheets

(56) References Cited

U.S. PATENT DOCUMENTS

| | | | |
|---|---|---|---|
| 3,118,448 | A | 1/1964 | Gottschalk |
| 3,135,993 | A | 6/1964 | Ryan |
| 3,179,107 | A * | 4/1965 | Clark .......................... 604/242 |
| 3,330,004 | A | 7/1967 | Cloyd |
| 3,359,619 | A | 12/1967 | Walkden |
| 3,470,604 | A | 10/1969 | Zenick |
| 3,648,684 | A | 3/1972 | Barnwell et al. |
| 3,756,235 | A | 9/1973 | Burke et al. |
| 3,782,383 | A | 1/1974 | Thompson et al. |
| 3,865,236 | A | 2/1975 | Rycroft |
| D238,617 | S | 1/1976 | Evanston |
| 3,943,225 | A | 3/1976 | Koehn |
| 4,003,262 | A | 1/1977 | Gerarde et al. |
| 4,070,756 | A | 1/1978 | Shields |
| 4,263,922 | A | 4/1981 | White |
| D262,739 | S | 1/1982 | Nitshke |
| 4,367,738 | A | 1/1983 | Legendre et al. |
| 4,367,749 | A | 1/1983 | Dudley et al. |
| 4,391,273 | A | 7/1983 | Chiquiar-Arias |
| 4,392,497 | A | 7/1983 | Ghaussy |
| 4,441,951 | A | 4/1984 | Christinger |
| 4,513,754 | A | 4/1985 | Lee |
| 4,581,024 | A | 4/1986 | Swenson |
| 4,585,444 | A | 4/1986 | Harris |
| 4,589,871 | A | 5/1986 | Imbert |
| 4,617,012 | A | 10/1986 | Vaillancourt |
| 4,655,764 | A | 4/1987 | Sato |
| 4,675,007 | A | 6/1987 | Terry |
| 4,742,910 | A | 5/1988 | Staebler |
| 4,795,445 | A | 1/1989 | Jensen |
| 4,838,877 | A | 6/1989 | Massau |
| 4,840,185 | A | 6/1989 | Hernandez |
| 4,886,072 | A | 12/1989 | Percarpio et al. |
| 4,915,225 | A | 4/1990 | Tabor, Jr. et al. |
| 4,922,602 | A | 5/1990 | Mehl |
| 4,936,833 | A | 6/1990 | Sams |
| 4,972,843 | A | 11/1990 | Broden |
| 4,976,925 | A | 12/1990 | Porcher et al. |
| 5,026,355 | A | 6/1991 | Sweeney et al. |
| D321,759 | S | 11/1991 | Buswell et al. |
| 5,087,249 | A | 2/1992 | Deal |
| 5,125,058 | A | 6/1992 | Tenerz et al. |
| 5,183,469 | A | 2/1993 | Capaccio |
| 5,312,351 | A | 5/1994 | Gerrone |
| 5,364,369 | A | 11/1994 | Reynolds et al. |
| 5,489,272 | A | 2/1996 | Wirtz |
| 5,510,065 | A | 4/1996 | McFarlane |
| 5,529,189 | A | 6/1996 | Feldschuh |
| D377,687 | S | 1/1997 | Udovch |
| 5,607,399 | A | 3/1997 | Grimard et al. |
| 5,616,136 | A | 4/1997 | Shillington et al. |
| 5,667,495 | A | 9/1997 | Bitdinger et al. |
| D387,425 | S | 12/1997 | Niedospial et al. |
| 5,693,028 | A | 12/1997 | Shillington |
| 5,700,247 | A | 12/1997 | Grimard et al. |
| 5,803,918 | A | 9/1998 | Vetter et al. |
| D403,761 | S | 1/1999 | Adams |
| 5,980,495 | A | 11/1999 | Heinz et al. |
| D417,730 | S | 12/1999 | Brassil et al. |
| 5,997,511 | A | 12/1999 | Curie et al. |
| D419,671 | S | 1/2000 | Jansen |
| 6,223,408 | B1 | 5/2001 | Vetter et al. |
| 6,331,174 | B1 | 12/2001 | Reinhard et al. |
| 6,361,525 | B2 | 3/2002 | Capes et al. |
| 6,494,892 | B1 | 12/2002 | Ireland et al. |
| 6,537,259 | B1 | 3/2003 | Niermann |
| 6,558,353 | B2 | 5/2003 | Zohmann |
| D476,417 | S | 6/2003 | Swenson et al. |
| 6,589,261 | B1 | 7/2003 | Abulhaj et al. |
| 6,616,639 | B2 | 9/2003 | Gagnieux et al. |
| 6,629,962 | B2 | 10/2003 | Correa et al. |
| 6,709,428 | B2 | 3/2004 | Sagstetter |
| 6,723,111 | B2 | 4/2004 | Abulhaj et al. |
| D490,517 | S | 5/2004 | Harmon |
| D492,404 | S | 6/2004 | Prais et al. |
| RE38,964 | E | 1/2006 | Shillington |
| 7,024,749 | B2 | 4/2006 | Sagstetter |
| D558,340 | S | 12/2007 | Hochman et al. |
| 7,418,880 | B1 | 9/2008 | Smith |
| D578,210 | S | 10/2008 | Muta et al. |
| 7,455,661 | B2 | 11/2008 | Barrelle et al. |
| D588,693 | S | 3/2009 | Strong et al. |
| 7,544,189 | B2 | 6/2009 | Griffiths |
| 7,582,073 | B2 | 9/2009 | Barrelle et al. |
| D609,333 | S | 2/2010 | Holmes |
| D617,453 | S | 6/2010 | Shaw |
| 7,874,827 | B2 | 1/2011 | Togashi et al. |
| D635,249 | S | 3/2011 | Becker |
| D638,122 | S | 5/2011 | Kosinski et al. |
| 8,002,754 | B2 | 8/2011 | Kawamura et al. |
| 8,021,511 | B2 | 9/2011 | Erskine |
| D650,903 | S | 12/2011 | Kosinski et al. |
| 8,105,294 | B2 | 1/2012 | Araki et al. |
| 8,313,954 | B2 | 11/2012 | Leach et al. |
| 2001/0049496 | A1 | 12/2001 | Kirchhofer et al. |
| 2002/0007147 | A1 * | 1/2002 | Capes et al. .................. 604/110 |
| 2002/0026146 | A1 | 2/2002 | Jansen et al. |
| 2002/0133184 | A1 | 9/2002 | LoRusso |
| 2003/0069544 | A1 | 4/2003 | Lee |
| 2003/0088215 | A1 | 5/2003 | Ferguson et al. |
| 2003/0088234 | A1 | 5/2003 | Sagstetter |
| 2004/0002713 | A1 | 1/2004 | Olson et al. |
| 2004/0127857 | A1 | 7/2004 | Shemesh et al. |
| 2006/0079848 | A1 | 4/2006 | Pelkey et al. |
| 2006/0200085 | A1 | 9/2006 | Watts et al. |
| 2006/0200095 | A1 | 9/2006 | Steube |
| 2006/0247583 | A1 | 11/2006 | Klint et al. |
| 2007/0167912 | A1 | 7/2007 | Causey et al. |
| 2007/0185460 | A1 | 8/2007 | Vedrine et al. |
| 2007/0239117 | A1 | 10/2007 | Chelak et al. |
| 2007/0265582 | A1 | 11/2007 | Kaplan et al. |
| 2007/0286881 | A1 | 12/2007 | Burkinshsw |
| 2008/0183137 | A1 | 7/2008 | Barrelle et al. |
| 2008/0269688 | A1 | 10/2008 | Colucci et al. |
| 2009/0157044 | A1 | 6/2009 | Liyanagama et al. |
| 2010/0152678 | A1 | 6/2010 | Jakob |
| 2010/0270702 | A1 | 10/2010 | Zelkovich et al. |
| 2012/0022457 | A1 | 1/2012 | Silver |
| 2012/0078179 | A1 | 3/2012 | Finke |
| 2013/0138047 | A1 | 5/2013 | Takemoto et al. |

FOREIGN PATENT DOCUMENTS

| | | |
|---|---|---|
| CN | 1533289 A | 9/2004 |
| EP | 0350792 | 1/1990 |
| EP | 1291035 A2 * | 3/2003 |
| GB | 614003 A | 12/1948 |
| GB | 1207229 A | 9/1970 |
| JP | 4303730 | 10/1992 |
| WO | 2012043544 A1 | 4/2012 |

OTHER PUBLICATIONS

International Search Report Issued Oct. 22, 2009 in Int'l Appln. No. PCT/US2009/031112; Written Opinion.
Office Action issued Sep. 21, 2009 in U.S. Appl. No. 29/334,048.
Office Action issued Mar. 18, 2010 in U.S. Appl. No. 29/334,048.
Office Action issued Apr. 23, 2013 in U.S. Appl. No. 29/402,109.
U.S. Appl. No. 29/402,109 by Lundquist, filed Sep. 21, 2011.
Office Action issued Jul. 31, 2012 in JP Application No. 2010-543235.
Extended search report issued Jun. 12, 2012 in EP Application No. 12166374.4.
Extended search report issued Sep. 7, 2011 in EP Application No. 09702776.7.
U.S. Appl. No. 29/427,516 by Lundquist, filed Jul. 19, 2012.
Office Action issued Nov. 15, 2012 in U.S. Appl. No. 12/680,609.
Office Action issued Nov. 26, 2012 in CN Application No. 200980101066.7.
Office Action issued May 22, 2013 in CN Application No. 201210236911.5.

* cited by examiner

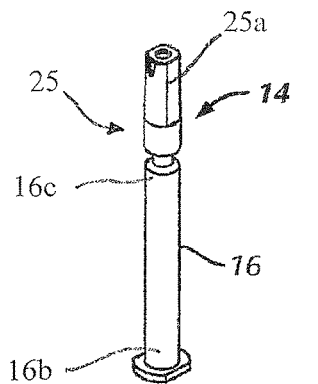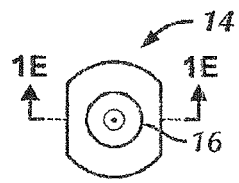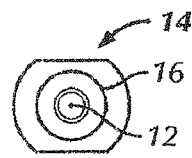
FIG. 1A  FIG. 1B  FIG. 1C
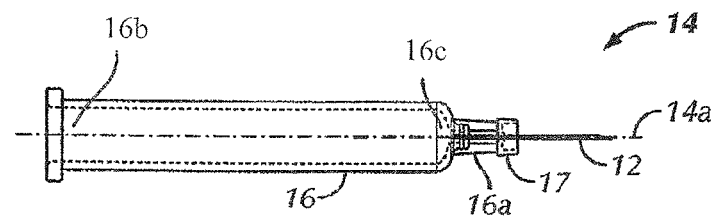
FIG. 1D
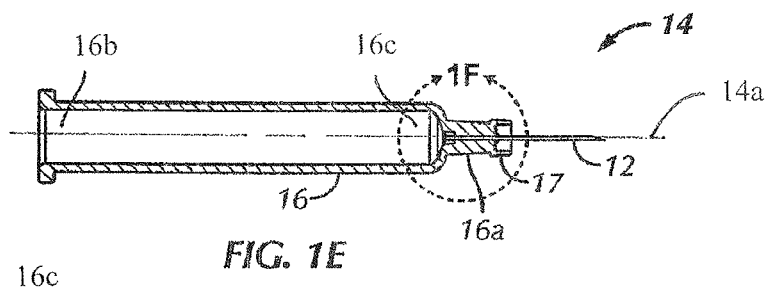
FIG. 1E
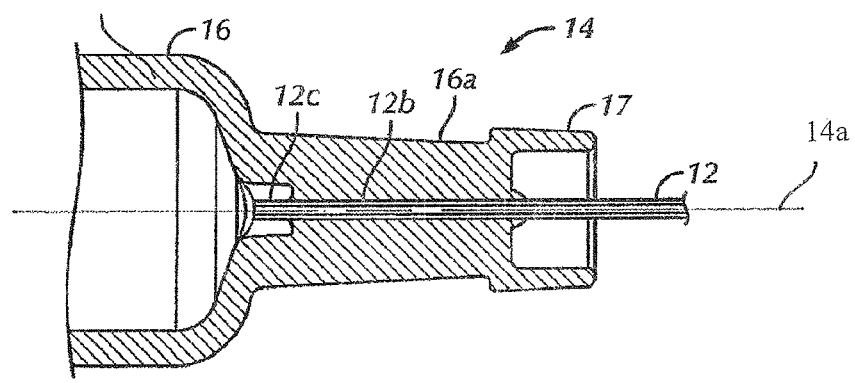
FIG. 1F

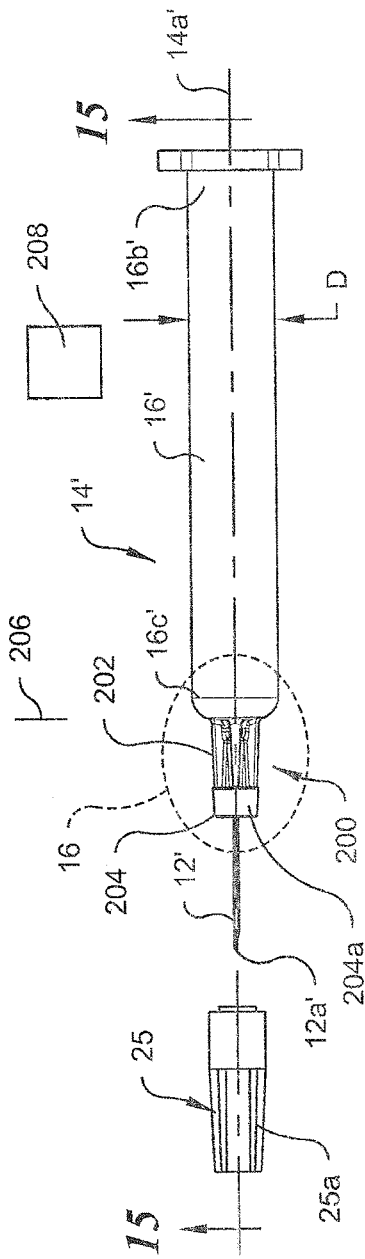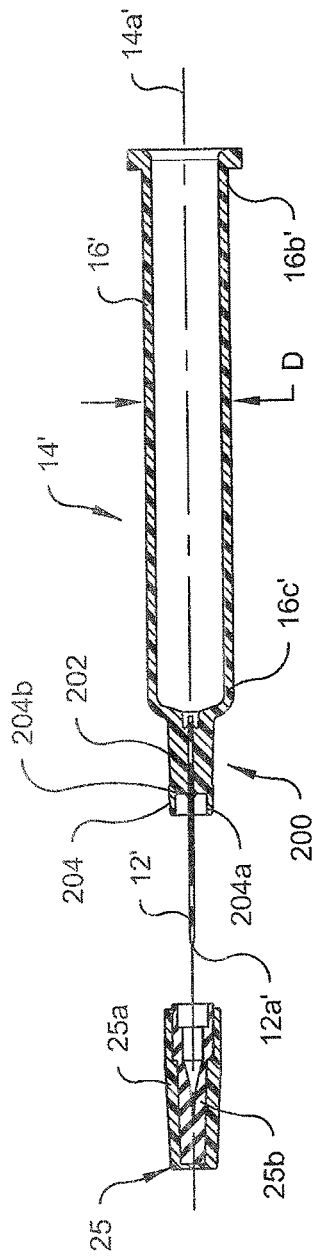
Fig. 14
Fig. 15

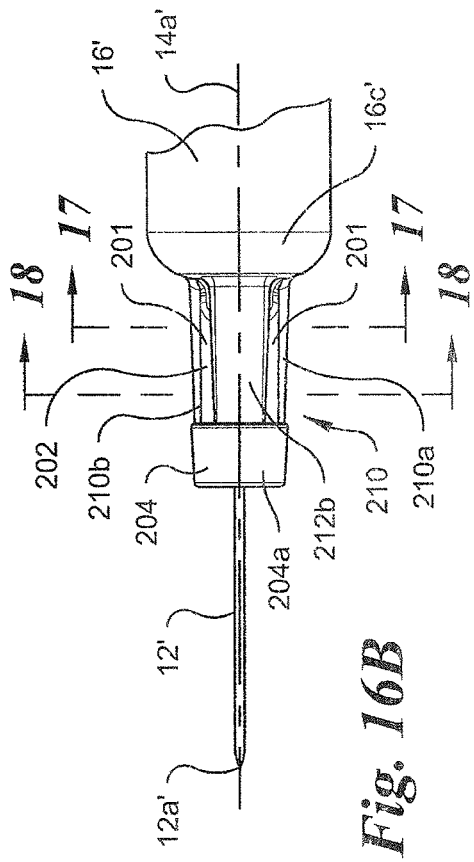
Fig. 16B
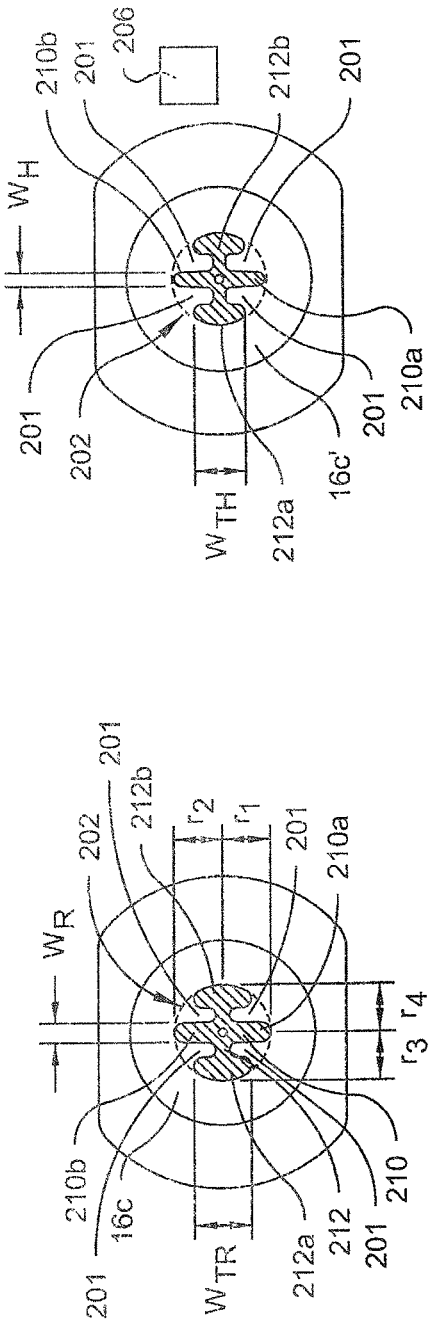
Fig. 17
Fig. 18

SYRINGE WITH CO-MOLDED HUB AND CANNULA

CROSS-REFERENCE TO RELATED APPLICATIONS

This application is a continuation-in-part application of U.S. patent application Ser. No. 12/680,609, filed Mar. 29, 2010, which is a Section 371 of International Application No. PCT/US09/031112, filed Jan. 15, 2009, which was published in the English language on Jul. 23, 2009 under International Publication No. WO 2009/091895 A2 and claims priority to U.S. Provisional Patent Application No. 61/021,186, filed Jan. 15, 2008, the disclosures of which are incorporated herein by reference in their entirety.

BACKGROUND OF THE INVENTION

The present invention relates to a hub for a syringe that is co-molded with a cannula and a method for forming or co-molding the cannula to the syringe barrel. The cannula is preferably a fine gauge cannula, which is co-molded to the syringe barrel to form a staked needle device.

The process of bonding a cannula to a syringe barrel involves precisely positioning and then bonding the cannula to the syringe without damaging the cannula. Bends or buns in the cannula resulting from the manufacturing process can increase perceived pain of the patient. The cannula is preferably co-axial with the center or longitudinal axis of the syringe. The cannula is also preferably bonded to the syringe to withstand an approximately twenty-two Newton (22N) pull test rating in accordance with the International Standards Organization's (ISO's) standards.

The cannula of a syringe having a polymeric barrel is traditionally interference fit into a preformed barrel utilizing techniques similar to those used to manufacture syringes having glass barrels. The cannula is often affixed to the syringe by an adhesive when utilizing this method. Adhesive bonding to affix a cannula to the barrel of the syringe may be undesirable in certain situations because the adhesive may contain chemicals that could leach into the medication in the syringe. The medication may be prefilled in to the syringe, resulting in potentially prolonged exposure of the medication to the adhesive. The leaching chemicals of the adhesive may have an adverse impact on the medication/biological compound(s) maintained in the barrel of the syringe, such as altering the efficacy and/or stability of the syringe contents that eventually enter the patient.

In order to avoid the use of an adhesive, the cannula is typically crimped near its proximal end and the syringe barrel is insert molded over the proximal end of the cannula so that the syringe molds over the crimped proximal end to securely grip and retain the cannula. Though crimping the proximal end may avoid the use of an adhesive, relatively fine gauge cannulas, for example twenty-seven to thirty (27-30) gauge cannulas cannot usually be crimped without potentially damaging the cannula due to their small physical dimensions. Regardless of the attachment method, it is difficult to position, hold, and/or mount a fragile, fine gauge cannula without damaging the cannula.

It would be desirable to design, construct and employ a mechanism that holds the cannula, particularly a small diameter cannula, during the insert molding process to attach the cannula directly to a polymeric syringe barrel without the use of an adhesive or the need to crimp the cannula and without damaging the cannula. It is also desirable to construct a hub at the distal end of the barrel that effectively secures the cannula to the barrel and provides sufficient strength to withstand the operating conditions of the syringe, while utilizing a cost-effective and efficient manufacturing process.

BRIEF SUMMARY OF THE INVENTION

Briefly stated, the present application is directed to a prefilled syringe for injecting medicament into a patient including a barrel constructed of a polymeric material, a cannula and a hub. The barrel has a diameter, a longitudinal axis, a proximal end and a distal end. The cannula has a root end and a tip opposite the root end. The root end is fixed to the distal end of the barrel. The cannula is positioned generally coaxially with the longitudinal axis. The hub is integrally formed or co-molded with the distal end. The hub includes a rib section and a cap. The rib section has a generally cruciform cross-section taken along a rib plane that is generally perpendicular to the longitudinal axis. The cap has a generally U-shaped cross-section taken along a longitudinal plane that is generally parallel to the longitudinal axis.

In another aspect, the present application is directed to a prefilled syringe for injecting medicament into a patient. The syringe includes a barrel constructed of a polymeric material, a cannula and a hub. The barrel has a diameter, a longitudinal axis, a proximal end and a distal end. The cannula has a root end and a tip opposite the root end. The root end is fixed to the distal end of the barrel. The cannula is positioned generally coaxially with the longitudinal axis. The hub is integrally formed with the distal end. The hub includes a rib section and a cap. The rib section includes a first pair of ribs and a second pair of ribs. The first pair of ribs has a generally H-shaped cross-section and the second pair of ribs has a generally rectangular-shaped cross-section. The cannula is co-molded with the rib section.

BRIEF DESCRIPTION OF THE SEVERAL VIEWS OF THE DRAWINGS

The following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1A is a perspective view of a staked needle formed through the use of a collet mechanism in accordance with a first preferred embodiment of the present invention;

FIG. 1B is an enlarged rear elevational view of the staked needle shown in FIG. 1A;

FIG. 1C is an enlarged front elevational view of the staked needle shown in FIG. 1A;

FIG. 1D is a side elevational view of the staked needle shown in FIG. 1A;

FIG. 1E is an enlarged cross-sectional view of the staked needle shown in FIG. 1A taken from within circle 1F of FIG. 1B;

FIG. 1F is a greatly enlarged cross-sectional view of the needle end of the staked needle shown in FIG. 1A taken from within circle 1F of FIG. 1E;

FIG. 14 is a left-side elevational view of a syringe in accordance with a third preferred embodiment of the present invention;

FIG. 15 is a cross-sectional view of the syringe of FIG. 14, taken along line 15-15 of FIG. 14;

FIG. 16B is a magnified left-side elevational view of a distal end portion of the syringe of FIG. 14, taken from within dashed circle 16 of FIG. 14;

FIG. 17 is a cross-sectional view of a rib section of the syringe of FIG. 14, taken along line 17-17 of FIG. 16B; and FIG. 18 is a cross-sectional view of the rib section of the syringe of FIG. 14, taken along line 18-18 of FIG. 16B.

DETAILED DESCRIPTION OF THE INVENTION

Figure 2A:
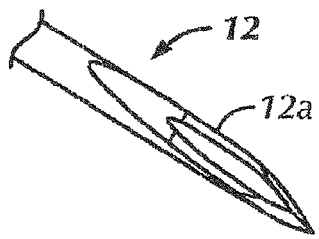
FIG. 2A is a greatly enlarged perspective view of a needle tip of the staked needle shown in FIG. 1A.
Figure 2B:
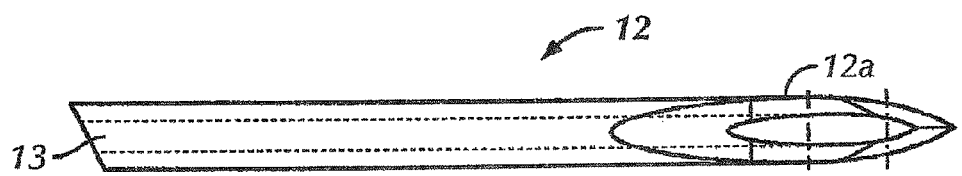
FIG. 2B is a greatly enlarged side elevational view of the needle tip shown in FIG. 2A.
Figure 2C:
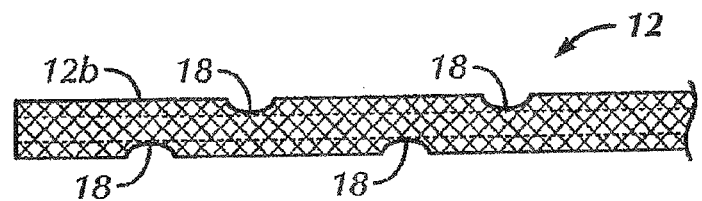
FIG. 2C is a greatly enlarged side elevational view of the proximal end of the needle shown in FIG. 2A.
Figure 3:
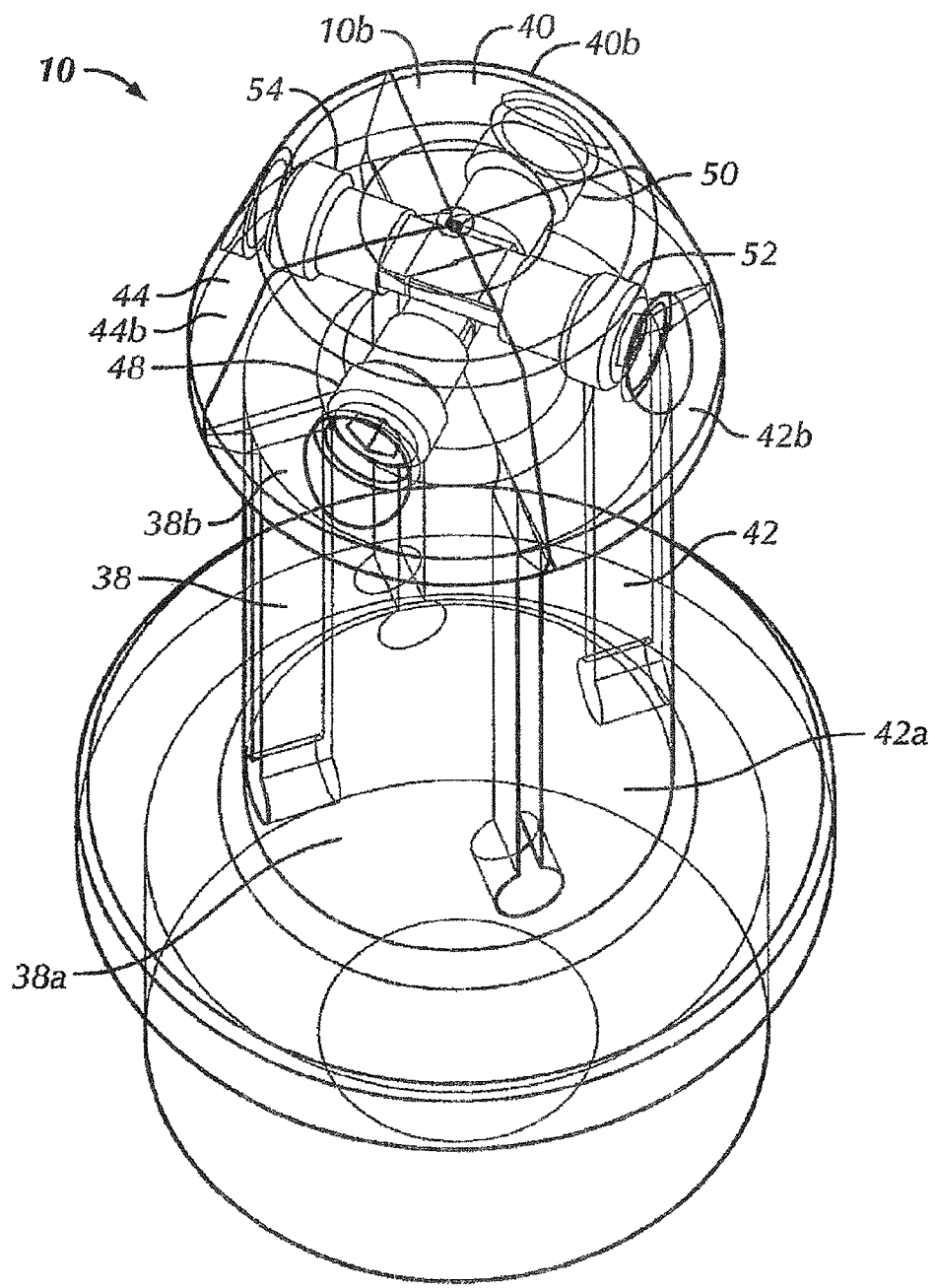
FIG. 3 is a semi-transparent perspective view of a collect mechanism in accordance with the first preferred embodiment of the present invention.
Figure 4:
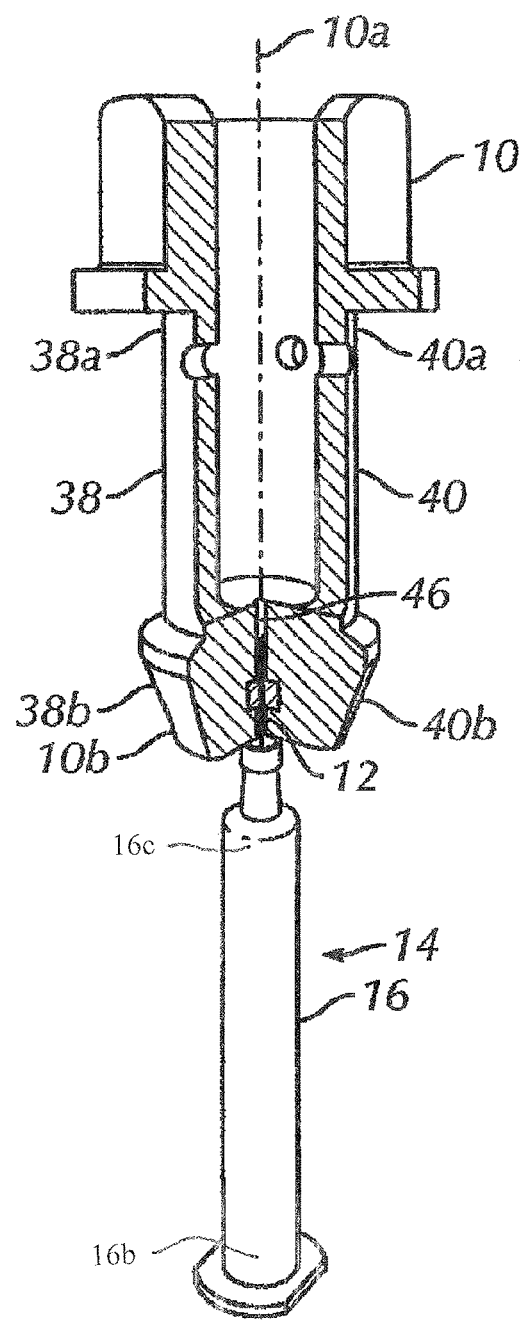
FIG. 4 is a perspective view of a partial collect mechanism shown in FIG. 3 following injection molding with the mold removed.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center or orientation of the syringe and related parts thereof. Unless specifically set forth herein, the terms "a", "an" and "the" are not limited to one element but instead should be read as meaning "at least one". The terminology includes the words noted above, derivatives thereof and words of similar import.

Referring to the drawings, wherein like numerals indicate like elements throughout, there is shown in FIGS. 3-7 and 11-13 a first preferred embodiment of a collet mechanism 10. The collet mechanism 10 is used to position and hold a cannula 12 in place during insert molding of a staked needle or syringe, generally 14, without damaging the cannula 12.

Referring to FIGS. 1A-2C and 14, the staked needle or syringe 14, 14' is constructed of a polymeric barrel 16, 16' that is directly insert molded over the cannula 12, 12'. The syringe 14' of the third preferred embodiment has similar features to the syringe 14 of the first preferred embodiment and like reference numerals are utilized to identify like elements of the syringes 14, 14' of the first and third embodiments with the prime symbol (') utilized to distinguish the elements of the third preferred embodiment from the elements of the first preferred embodiment. The barrel 16, 16' is preferably constructed of a transparent cyclic olefin copolymer or polymer (COC or COP). The hub 200 or distal tip 16a of the barrel 16, 16' extends over and is preferably co-molded with a proximal end 12b of the cannula 12, 12'. The cannula 12, 12' is to be attached to the distal tip 16a or hub 200 of the barrel 16, 16' that is directly insert molded over the cannula 12, 12'. The distal end 17 or hub 200 is generally hollow, so as to form a sleeve around the cannula 12, 12' (FIGS. 1E, 1F and 14). Hollowing out the interior of the distal end 17 or hub 200 around the cannula 12, 12' reduces the amount of polymeric material in contact with the cannula 12, 12' and therefore further reduces the cooling time required for the insert molding process, as described below. The hub 200 is sufficiently sized and tapered to allow for a cannula or needle shield 25, generally manufactured for use with staked glass needles, to attach to the hub 200. Specifically, the needle shield 25 is preferably removably mountable to a cap 204 of the hub 200.

Referring specifically to FIGS. 2A-2C and 14, the cannula 12, 12' is preferably a fine gauge hollow metallic needle, for example, a twenty-seven to thirty (27-30) gauge needle. The twenty-seven (27) gauge needle or cannula 12, 12' typically has a nominal outer diameter of sixteen thousandths inches to one hundred sixty-five hundred thousands inches (0.0160-0.0165 in) and a nominal inner diameter of seventy-five hundred thousandths inches to ninety hundred thousandths inches (0.0075-0.0090 in). A thirty (30) gauge needle or cannula 12, 12' typically has a nominal outer diameter of one hundred twenty hundred thousandths inches to one hundred twenty-five hundred thousandths inches (0.0120-0.0125 in) and a nominal inner diameter of fifty-five hundred thousandths inches to seventy hundred thousandths inches (0.0055-0.0070 in). The interior lumen 13 of the cannula 12, 12' is preferably straight. The cannula 12, 12' preferably has a tip 12a, 12a' with a three-bevel grind, meaning that the tip 12a, 12a' is tapered at three distinct angles to reduce the pain perceived by a patient. However, the tip 12a, 12a' is not limited to being three-bevel ground and may have nearly any configuration and shape that is able to be inserted into the patient for delivery of the medicament into the patient.

A plurality of notches 18 are preferably formed on the outer surface of the proximal end 12b of the cannula 12, 12'. The notches 18 preferably extend radially inwardly and are axially spaced apart from each other. The notches 18 are preferably machined into the proximal end 12b of the cannula 12, 12'. The notches 18 aid in affixing or securing the proximal end 12b of the cannula 12, 12' to the tip 16a or hub 200 of the barrel 16, 16' because the polymeric material forming the distal end 17 or hub 200 flows into and fills in the notches 18 during the molding process, as described below, to provide enhanced friction and gripping force between the proximal end 12b and the distal end 17 or hub 200. Because the cannula 12, 12' may generally not be crimped without potentially damaging the cannula 12, 12' due to its size, the notches 18, which are formed in the cannula 12, 12' generally replace the function of crimping the cannula 12, 12'. As shown in FIG. 1F, a portion 12c of the proximal end 12b of the cannula 12, 12' extends into a hollow of the barrel 16, 16' due to the molding process, as described further below. At least a portion of the proximal end 12b of the cannula 12, 12' may be textured or roughened (shown in FIG. 2C with cross hatching) by a mechanical or chemical surface treatment to further enhance the gripping force of the proximal end 12b of the cannula 12, 12' and to better secure the proximal end 12b to the distal end 17 or hub 200 near the barrel 16, 16'. Though the above described cannula 12, 12' is preferred, it is within the spirit and scope of the present invention that any sized and shaped cannula 12, 12' may be used.

Referring specifically to FIGS. 3-5B, the collet mechanism 10 has first and second axially extending flexible arms 38, 40 that form an expandable internal cavity 46 (see FIGS. 6 and 12), but may include any number of flexible arms. Preferably, the collet mechanism 10 further includes third and fourth flexible arms 42, 44. Each flexible arm 38, 40, 42. 44 has an attached proximal end 38a, 40a, 42a (the proximal end of the fourth flexible arm 44 obstructed from view) and a free or unattached distal end 38b, 40b, 42b, 44b. The flexible arms 38, 40, 42, 44 may be flexed inwardly and outwardly with the greatest deflection occurring toward the distal ends 38b, 40b, 42b, 44b. The flexible arms 38, 40, 42, 44 are in a closed position (FIGS. 3 and 7) when the distal ends 38b, 40b, 42b, 44b are flexed inwardly, towards the internal cavity 46. The flexible arms 38, 40, 42, 44 are in an open position (FIG. 6) when the distal ends 38b, 40b, 42b, 44b of the flexible arms 38, 40, 42, 44 are positioned away from the internal cavity 46 (e.g., flexed outwardly). The open position of the collet mechanism 10 is preferably the unrestrained state, meaning that the distal ends 38b, 40b, 42b, 44b are untouched, and the closed position of the collet mechanism 10 is preferably the restrained position, meaning that the distal ends 38b, 40b, 42b, 44b are forced together by an outside force, though the opposite configuration may be used if desired.

Figure 5A:
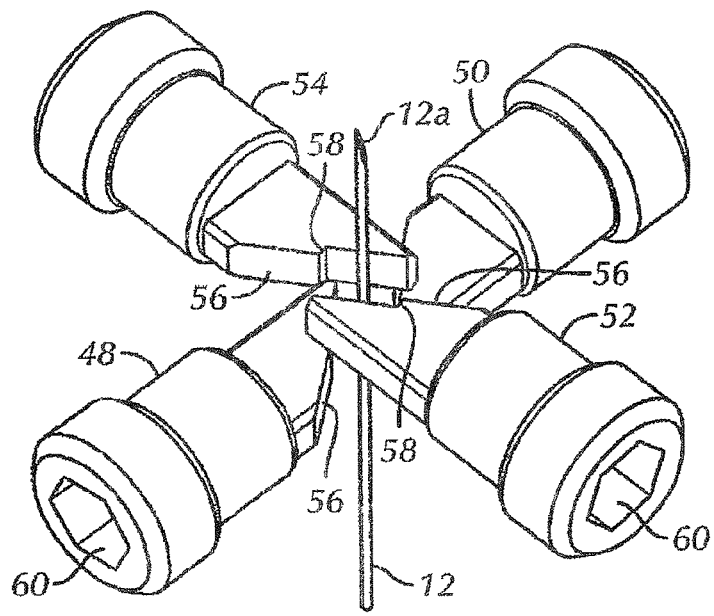
FIG. 5A is a greatly enlarged perspective view of cannula guides of the collet mechanism shown in FIG. 3 in an open position.
Figure 5B:
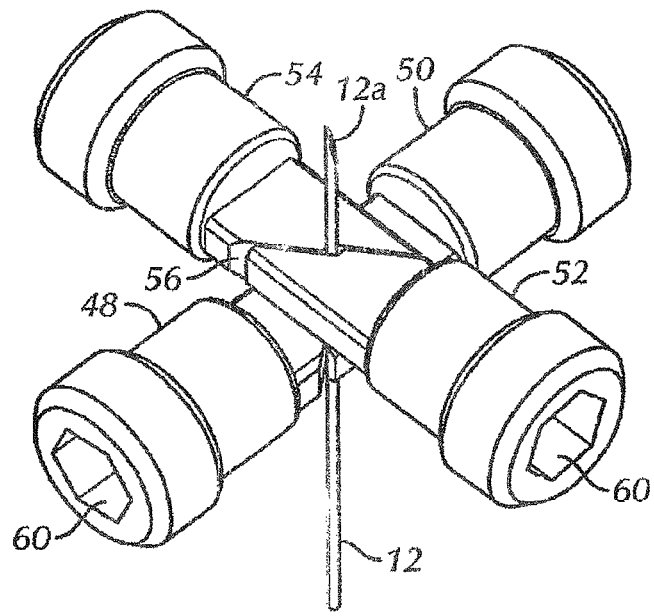
FIG. 5B is a greatly enlarged perspective view of the cannula guides shown in FIG. 5A in a closed position.
Figure 6:
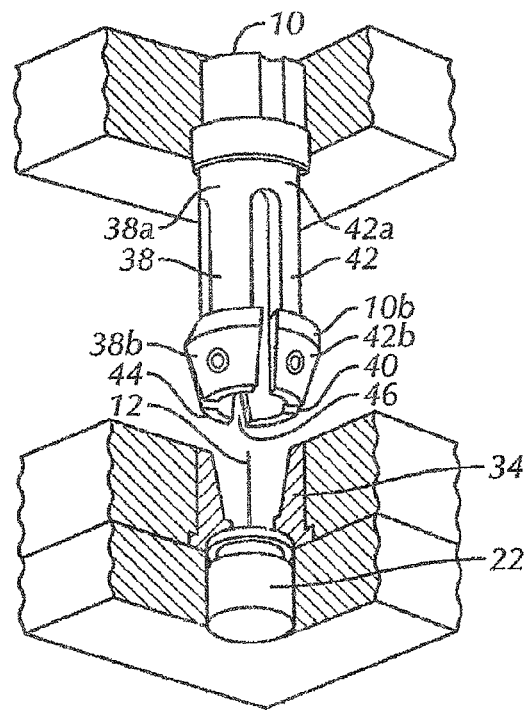
FIG. 6 a perspective schematic view of the collect mechanism and a portion of the mold in an open position.
Figure 7:
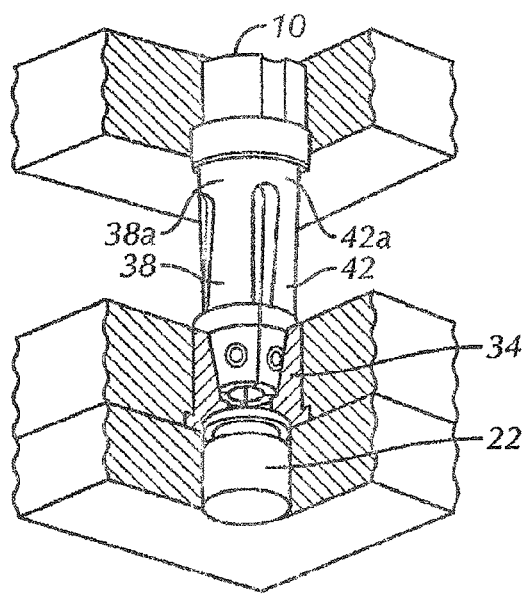
FIG. 7 is a perspective schematic view of the collect mechanism and a portion of the mold shown in FIG. 6 in a closed position.

Referring specifically to FIGS. 5A and 5B, the first and second flexible arms 38, 40 include first and second cannula guides 48, 50, respectively. The first cannula guide 48 is preferably directly opposed from the second cannula guide 50. Preferably, the third and fourth flexible arms 42, 44 include third and fourth cannula guides 52, 54, respectively, the third cannula guide 52 preferably being directly opposed from the fourth cannula guide 54. The cannula guides 48, 50, 52, 54 are preferably comprised of a polytetrafluoroethylene material, a plastic with nonstick properties such as TEFLON®, that is gentle on the cannula 12, but resists the elevated temperature of the mold 20. However, the cannula guides 48, 50, 52, 54 may be comprised of any heat resistant polymeric material or a stainless steel.

The cannula guides 48, 50, 52, 54 are mounted proximate and positioned through the distal ends 38, 40, 42, 44 of the respective flexible arms 38, 40, 42, 44 and extend radially at least partially into the expandable internal cavity 46. The cannula guides 48, 50, 52, 54 are preferably generally orthogonal to the flexible arms 38. 40, 42, 44. The cannula guides 48, 50, 52, 54 clamp a portion of the cannula 12 to hold the cannula 12 in place when the flexible arms 38, 40, 42, 44 are in the closed position (FIG. 5B). The cannula guides 48, 50, 52, 54 are spaced away from the cannula 12 when the flexible arms 38, 40, 42, 44 are in the open position (FIG. 5A).

A position of the cannula guides 48, 50, 52, 54 is preferably adjustable with respect to the flexible arms 38, 40, 42, 44 and the internal cavity 46 with a tool, such as an Allen Wrench, by inserting the tool into an adjustment opening 60 of the cannula guides 48, 50, 52, 54 to position the cannula guides 48, 50, 52, 54 at a predetermined depth into the internal cavity 46. Because the size of the cannula 12 may change and the size of the collet mechanism 10 may vary slightly, the adjustability of the position of the cannula guides 48, 50, 52, 54 allows a user to adjust and set the pressure exerted on the cannula 12 and the resulting force with which the cannula guides 48, 50, 52, 54 contact the cannula 12. Preferably, the position of the cannula guides 48, 50, 52, 54 may be adjusted in accordance with a predetermined force. Thus, one can ensure that the cannula guides 48, 50, 52, 54 sufficiently position and hold the cannula 12 in the desired position without damaging (i.e. bending, crimping or scratching) the cannula 12, but with sufficient force to retain the cannula 12 without allowing its movement during the injection or insert molding process. Preferably, the flexible arms 38, 40, 42, 44 exert a predetermined amount of force upon the cannula 12 when they are in the closed position and in contact with the cannula 12, such that the cannula 12 is not damaged and the sharpness of the tip 12a of the cannula 12 is not altered during the molding process. However, it is within the spirit and scope of the present invention that the cannula guides 48, 50, 52, 54 be immovably mounted to the respective flexible arm 38, 40, 42, 44.

Referring again to FIGS. 5A and 5B, each cannula guide 48, 50, 52, 54 preferably has a sloped mating surface 56 with an indentation or step 58 formed in the center, but may have any mating configuration, such as mating V-shaped members. As shown in FIG. 5B, as the flexible arms 38, 40, 42, 44 move into the closed position, the first and second cannula guides 48, 50 come into mating contact with each other and the third and fourth cannula guides 52, 54 come into mating contact with each other, and all of the cannula guides 48, 50, 52, 54 come into contact with the cannula 12, such that the cannula 12 slides along the sloped mating surface 56 into the indentation 58 of each of the cannula guides 48, 50, 52, 54. When the flexible arms 38, 40, 42, 44 are in the closed position, each indentation 58 abuts the cannula 12, such that the cannula 12 is positioned and held firmly along the center of the collet mechanism 10, generally in alignment with a central longitudinal axis 10a of the collet mechanism 10, and inline with the centerline or longitudinal axis 14a of the staked needle or syringe 14. The cannula guides 48, 50, 52, 54 may mate together in any manner, such as all four guides mating together, as long as the cannula 12 is sufficiently held in place during the injection or insert molding process.

Figure 8:
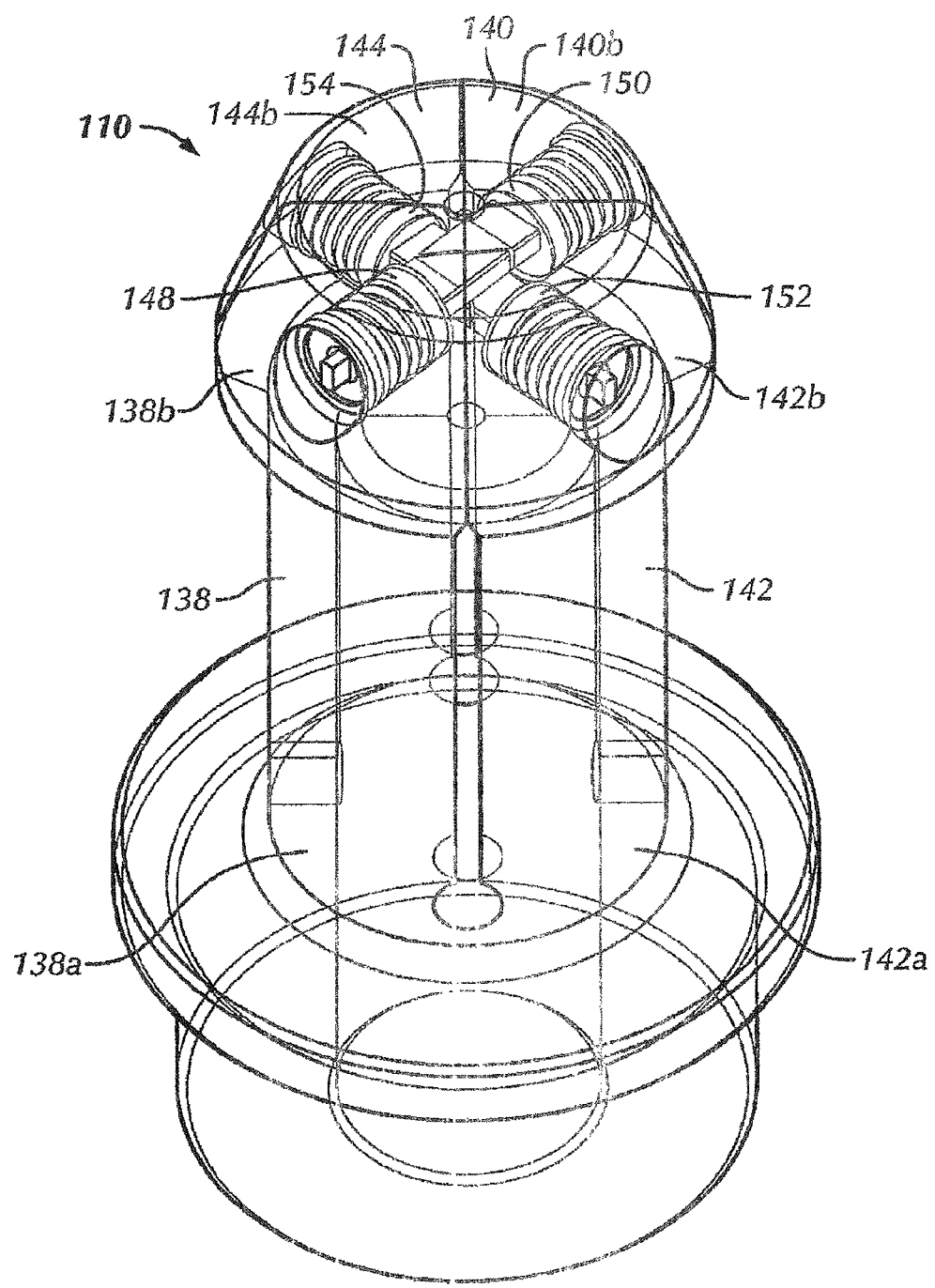
FIG. 8 is a semi-transparent perspective view of a collect mechanism in accordance with a second preferred embodiment of the present invention.
Figure 9:
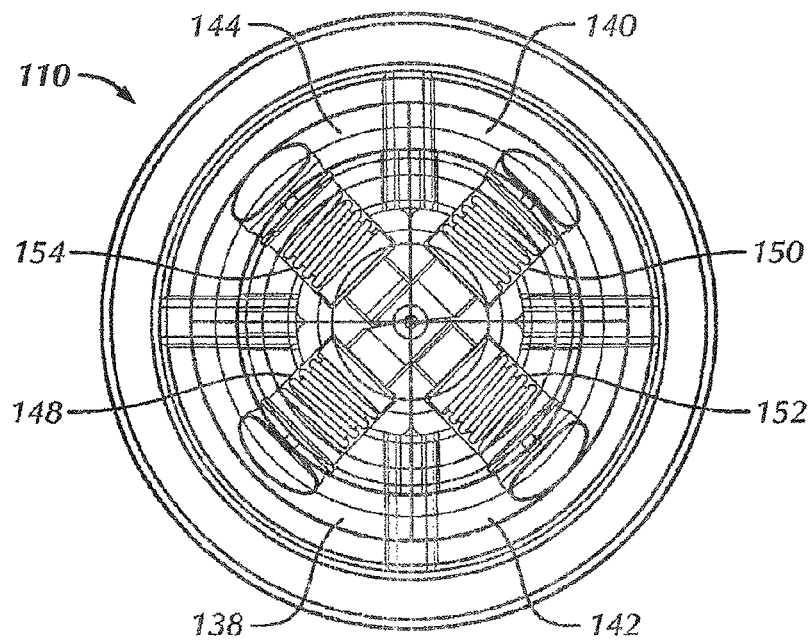
FIG. 9 is a top plan view of the collect mechanism shown in FIG. 8.
Figure 10:
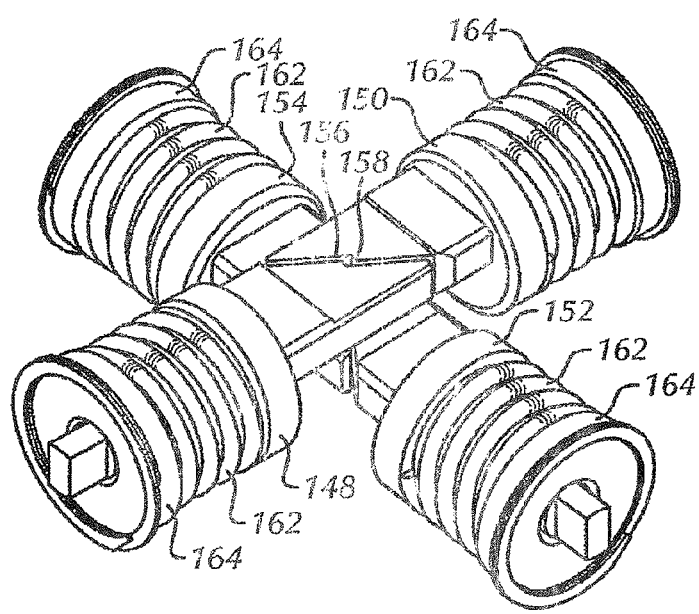
FIG. 10 is a perspective view of cannula guides of the collect mechanism shown in FIG. 8 in a closed position.

Referring to FIGS. 8-10, a second preferred embodiment of the collet mechanism 110 is shown. The collet mechanism 110 is similar to the first preferred embodiment of the collet mechanism 10, except that the cannula guides 148, 150, 152, 154 are each spring biased toward the open position. Preferably, each cannula guide 148, 150, 152, 154 includes a coil spring 162 to inwardly spring bias the cannula guides 148, 150, 152, 154. The collect mechanism 110 includes similar elements to the collect mechanism 10 and such elements have been similarly numbered with the addition of a leading one (1). A mounting member 164 is secured to the distal ends 138b, 140b, 142b, 144b of each of the flexible arms 138, 140, 142, 144. The coil springs 162 are positioned between the mounting members 164 and the cannula guides 148, 150, 152, 154 such that the cannula guides 148, 150, 152, 154 may accommodate differently sized cannulas 12 or may be used in order to ensure that the cannula guides 148, 150, 152, 154 contact and firmly hold the cannula 12 without the need for adjustment. The springs 162 are preferably replaceable such that the springs 162 having the desired pressure are used. It is within the spirit and scope of the present invention that the first and second embodiments of the collet mechanism 10, 110 be combined such that the cannula guides 48, 50, 52, 54 and 148, 150, 152, 154 may be both adjustable and spring biased.

Figure 11:
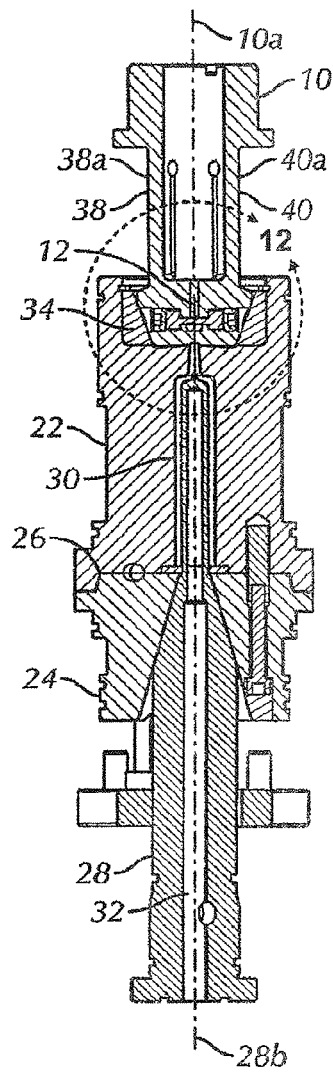
FIG. 11 is a cross sectional view of the collect mechanism shown in FIG. 3 and mold components.
Figure 12:
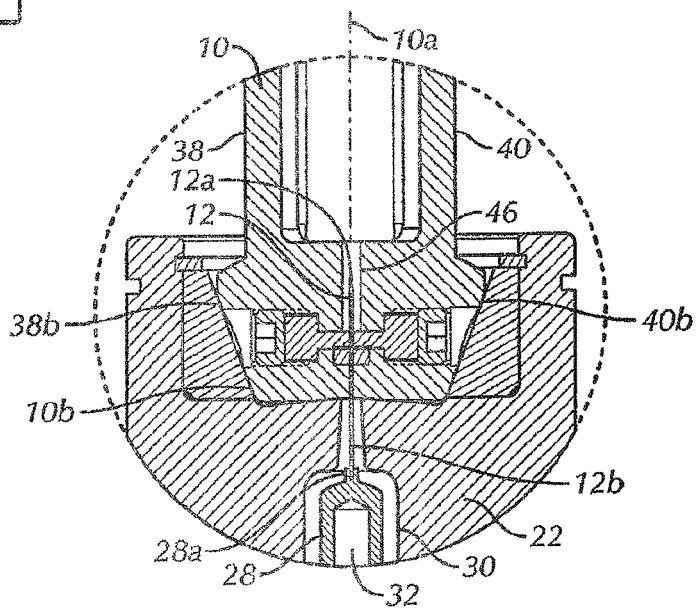
FIG. 12 is a greatly enlarged cross sectional view of the collect mechanism and mold shown in FIG. 11 taken within circle 12 of FIG. 11.
Figure 13:
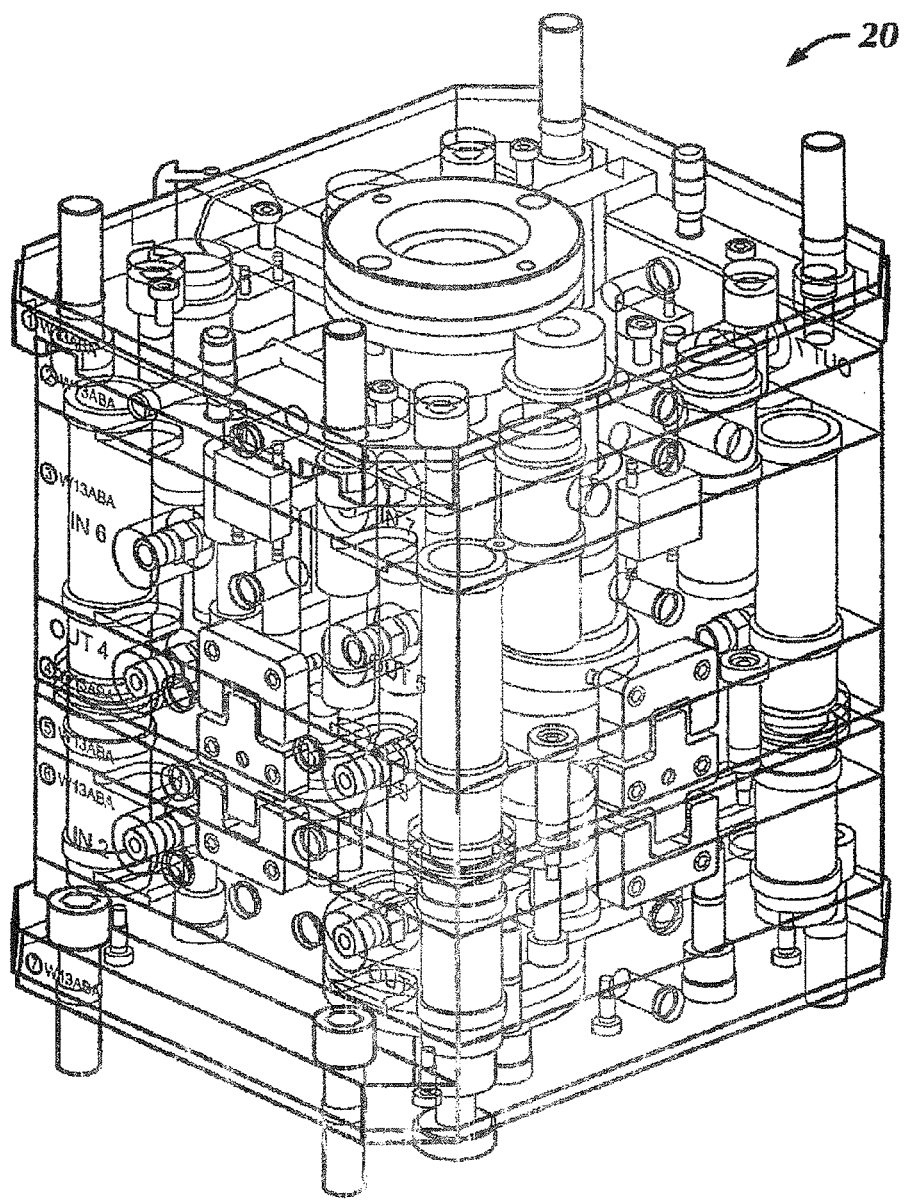
FIG. 13 is a semi-transparent perspective view of the mold encasement for the collet and mold components shown in FIG. 11.

Referring to FIGS. 1A-1F and 11-13, the staked needle or syringe 14, 14' is preferably manufactured in an insert mold 20 (FIG. 13). The insert mold 20 includes an A-side mold 22 and a B-side mold 24, separable along a parting line 26, shown in FIG. 11. A core member 28, preferably comprised of steel, extends from the B-side mold 24 upwardly and into a mold cavity 30 in the A-side mold 22. The mold cavity 30 is in the shape of the to-be-formed barrel 16, 16'. A cooling cavity 32 preferably extends through the center of the core member 28 to cool the core member 28 during molding. The A-side mold 22 includes a conically tapered receiving port 34 positioned above the core member 28 where the distal end 17 or hub 200 is to be formed. The tapered receiving port 34 at least partially surrounds a portion of the cannula 12, 12'.

Referring to FIGS. 6, 7, 11, 12 and 14, during molding of the staked needle or syringe 14, 14', a robotic arm (not shown) transports the cannula 12, 12' and places the proximal end 12b of the cannula 12, 12' onto a recessed tip 28a of the core member 28. The tip 28a of the core member 28 receives the portion 12c of the cannula 12, 12' and positions the cannula 12, 12' generally inline with a center line or longitudinal axis 14a, 14a' (see FIG. 1F) of the staked needle 14, 14'. The A-side mold 22 is inserted over the steel core member 28 such that the A-side mold 22 contacts the B-side mold 24 along the parting line 26. The tip 12a, 12a' of the cannula 12 extends at least partially through the receiving port 34.

Once the cannula 12, 12' and A-side mold 22 have been positioned on the core member 28, the collet mechanism 10, preferably having flexible arms 38, 40, 42, 44 with distal ends 38b, 40b, 42b, 44b, is inserted through the A-side mold 22 over the beveled tip 12a, 12a' of the cannula 12, 12', such that the distal end 10a of the collet mechanism 10 is guided by the tapered receiving port 34 to move the collet mechanism 10 into the closed position. More specifically, the distal ends 38b, 40b, 42b, 44b of the flexible arms 38, 40, 42, 44 are inserted into the tapered receiving port 34 which flexes the flexible arms 38, 40, 42, 44 towards the internal cavity 46 as the distal ends 38b, 40b, 42b, 44b slide along the taper of the tapered receiving port 34, until the collet mechanism 10 abuts the A-side mold 22. Once the collet mechanism 10 abuts the A-side mold 22, or is otherwise stopped, and the distal ends 38b, 40b, 42b, 44b are fully received in the receiving port 34 as shown in FIGS. 11 and 12, the collet mechanism 10 is in the closed position. In the closed position, the cannula guides 48, 50, 52, 54 clamp a portion of the cannula 12 to hold the cannula 12 generally in alignment with the central longitudinal axis 10a of the collet mechanism 10 and with a central longitudinal axis 28a of the core member 28. The cannula 12 extends beyond the distal ends 38b, 40b, 42b, 44b of the flexible arms 38, 40, 42, 44 and, thus, the collet mechanism 10 generally does not damage the beveled tip of the cannula 12. Further, in the closed position, the cannula 12 is positioned and firmly held in the center of the internal cavity 46 and is generally inline with the centerline or longitudinal axis 14a of the staked needle 14 (see FIG. 1D).

Referring specifically to FIG. 11, once the collet mechanism 10 is in place within the A-side mold 22 of the insert mold 20, molten polymeric material (not shown) is injected into the mold cavity 30 proximate the parting line 26 (dispensing line not shown) until the mold cavity 30 is completely filled with the molten polymeric material. The insert mold 20 operates at a temperature of approximately two hundred thirty degrees Fahrenheit (230° F.). The insert mold 20 remains closed and the molten polymeric material is allowed to cool to a substantially solidified state over at least the proximal end of the cannula 12. It may take approximately thirty seconds (30 sec.) for the polymeric material to substantially solidify. Once the polymeric material is cooled to a semi-hardened object, and preferably, a fully hardened object, the collet mechanism 10 and the A-side mold 22 are removed, such that the cannula guides 48, 50, 52, 54 release the cannula 12. The staked needle 14 and attached cannula 12 are then removed from the steel core member 28 by a robotic arm (not shown), and the polymeric material is allowed to further cool and solidify, if necessary, to a fully hardened object.

Referring to FIGS. 1A-1F and 14-18, the barrel 16' of the third preferred embodiment is constructed of a polymeric material and includes a diameter D, a longitudinal axis or center line 14a', a proximal end 16b', and a distal end 16c'. The barrel 16' is preferably constructed of a transparent cyclic olefin copolymer or a transparent cyclic olefin polymer. The barrel 16' is not limited to constructions of cyclic olefin copolymer or cyclic olefin polymer and may be constructed of nearly any polymeric material that may be molded into the general size and shape of the barrel 16' is able to take on the general size and shape of the barrel 16' and withstand the normal operating conditions of the barrel 16'. The barrel 16' includes a hollow section wherein the medicament is held prior to injection into the patient.

The cannula 12' of the third preferred embodiment has the proximal end 12b' with the tip 12a' opposite the proximal end 12b'. The proximal end 12b' is fixed to the distal end 16c' of the barrel 16'. The cannula 12 is positioned generally coaxially with the longitudinal axis 14a'. The cannula 12' of the third preferred embodiment preferably has a gauge of twenty-seven to thirty-three (27-33). The cannula 12' is not limited to being in the range of twenty-seven to thirty-three (27-33) gauge and may be nearly any size that may be mounted to the syringe 14' for injecting medicament into the patient. The cannula 12' of the third preferred embodiment is preferably twenty-seven to thirty-three (27-33) gauge as this size of cannula 12' is typically considered to have relatively small outer diameters when compared to typical syringe cannulas. The construction and configuration of the syringe 14' of the third preferred embodiment is relatively well adapted for small diameter cannulas 12'.

The syringe 14' of the third preferred embodiment also includes a hub 200 integrally formed with the distal end 16c'. The hub 200 is preferably constructed of the transparent cyclic olefin copolymer or the transparent cyclic olefin polymer materials, similar to or the same as the barrel 16'. The barrel 16' and hub 200 are preferably co-molded in the third preferred embodiment utilizing the method described in the present application. However, the barrel 16' and hub 200 are not limited to constructions utilizing cyclic olefin copolymer and/or cyclic olefin polymer and may be constructed of nearly any material that is able to take on the general size and shape of the hub 200 and barrel 16', withstand the normal operating conditions of the barrel 16' and hub 200 and facilitate contact between the medicament and surfaces of the hub 200 and barrel 16' without contaminating the medicament.

The hub 200 of the third preferred embodiment includes a rib section 202 and a cap 204. The rib section 202 and cap 204 are preferably co-molded with the barrel 16' and the cannula 12' utilizing the above-described molding method. The rib section 202 preferably provides strength to the hub 200 in each of axial, bending and twisting loads, without requiring a full cylindrical block of polymeric material around the proximal end 12b of the cannula 12, thereby reducing material costs for molding or constructing the hub 200. The cap 204 provides an attachment area for the needle shield 25. Specifically, the cap 24 provides an attachment area for removable mounting of the needle shield 25. In the third preferred embodiment, the cap 204 includes an upstanding wall 204a that extends generally parallel to the longitudinal axis 14a' and generally forms a complete cylinder tapered inwardly towards the longitudinal axis 14a' as it extends toward the tip 12a'. The upstanding wall 204a preferably forms a generally complete cylinder to which the needle shield 25 engages in a mounted position (FIG. 1A). Accordingly, when the needle shield 25 is mounted to the cap 204, even if medicament were to escape from the tip 12a', the medicament generally does not leak out of the boundaries of the needle shield 25 and cap 204. In the third preferred embodiment, the upstanding wall 204a, a base 204b and the needle shield 25 enclose the tip 12a' of the cannula 12' to contain the medicament therein and generally prevent its release while the needle shield 25 is mounted to the syringe 14'.

The rib section 202 of the hub 200 has a generally cruciform cross-section taken along a rib a plane 206 (FIGS. 17 and 18). The rib plane 206 is generally perpendicular to the longitudinal axis 14a'. The rib section 202 preferably has a cruciform cross-section along its entire length between the barrel 16' and the cap 204, but is not so limited and may have alternative cross-sectional shapes and configurations.

Referring to FIGS. 2C and 16-18, the rib section 202 of the third preferred embodiment includes a first pair of ribs 210 and a second pair of ribs 212. The first pair of ribs 210 include a first rectangular rib 210a and a second rectangular rib 210b that are positioned on opposite sides of the longitudinal axis 14a' relative to each other. The second pair of ribs 212 include a first T-shaped rib 212a and a second T-shaped rib 212b positioned on opposite sides of the longitudinal axis 14a' relative to each other. The first and second rectangular ribs 210a, 210b and first and second T-shaped ribs 212a, 212b are preferably positioned approximately ninety degrees)(90° relative to each other about the longitudinal axis 14a', respectively. The rib section 202 of the third preferred embodiment is not limited to inclusion of the first and second pair of ribs 210, 212 or the specific configurations shown in FIGS. 14-18. The rib section 202 may take on nearly any configuration of ribs that provide strength to the hub 200 and are able to withstand the normal operating conditions of the hub 200. For example, the rib section 202 may include a single rib extending radially outwardly from one side of the longitudinal axis 14a' or may contain nearly any number of plurality of ribs extending from the longitudinal axis 14a' that are fixed to the proximal end 12b of the cannula 12'.

Referring to FIGS. 17 and 18, in the third preferred embodiment, the first and second pair of ribs 210, 212 define longitudinal voids 201 that extend generally along the length of the rib section 202. The hub 200 and, therefore, the longitudinal voids 201 are formed by the A-side mold 22 and conically tapered receiving port 34 (please confirm) of the insert mold 20. The longitudinal voids 201 generally reduce the amount of polymeric material required to construct the hub 200 of the syringe 14' of the third preferred embodiment. However, this configuration provides sufficient strength at the hub 200 to prevent failure of the hub 200 during normal operating conditions.

The first rectangular rib 210a has a first radius $r_1$ and the second rectangular rib 210b has a second radius $r_2$. The first and second radii $r_1$, $r_2$ are both preferably measured from the longitudinal axis 14a' to an edge of the first and second rectangular ribs 210a, 210b furthest away from the longitudinal axis 14a'. The first radius $r_1$ is generally equal to the second radius $r_2$ in the third preferred embodiment. The rib section 202 preferably tapers slightly from its attachment to the barrel 16' to its attachment with the cap 204. Accordingly, the first radius $r_1$ may be slightly greater at an area where the rib section 202 attaches to the barrel 16' than at a section where the rib section 202 attaches to the cap 204 and likewise with the second rectangular rib 210b. However, the first radius $r_1$ is preferably equal to the second radius $r_2$ when measured from the same cross section taken at an individual rib plane 206.

The first T-shaped rib 212a has a third radius $r_3$ and a second T-shaped rib 212b has a fourth radius $r_4$ in the third preferred embodiment. The third radius $r_3$ is generally equal to the fourth radius $r_4$. Similar to the first and second rectangular ribs 210a, 210b, the first and second T-shaped ribs 212a, 212b taper in the rib section 202. Accordingly, the third radius $r_3$ may be slightly smaller proximate the cap 204 than near the barrel 16', but measurements of the third and fourth radii $r_3$, $r_4$ taken along the same rib plane 206 are relatively equal in the third preferred embodiment.

The first, second, third and fourth radii $r_1$, $r_2$, $r_3$, $r_4$ are all generally equal when taken along the same rib plane 206 in the rib section 202. The first, second, third and fourth radii $r_1$, $r_2$, $r_3$, $r_4$ are approximately two millimeters (2 mm) in the third preferred embodiment. However, the first, second, third and fourth radii $r_1$, $r_2$, $r_3$, $r_4$ are not limited to being generally equal when taken along the same rib plane 206 or to being two millimeters (2 mm) and may vary depending upon design requirements or specific requirements of a particular hub 200. For example, adapting the hub 200 to a medical container other than the preferred syringe 14' may result in the dimensions of the hub 200 being changed. Having relatively equal first, second third and fourth radii $r_1$, $r_2$, $r_3$, $r_4$ generally facilitates molding using the above-described methods, construction of the A-side mold 22 and the conically tapered receiving port 34, as well as facilitates the molding method for molding the hub 200 and syringe 14'.

Referring to FIGS. 17 and 18, the first rectangular rib 210a has a rectangular root width $W_R$ and a rectangular head width $W_H$. The rectangular root width $W_R$ is generally greater than the rectangular head width $W_H$. In the third preferred embodiment, the rectangular root width $W_R$ is approximately five to nine tenths millimeters (0.5-0.9 mm) and the rectangular head width $W_H$ is approximately twenty-five to sixty-five hundredths millimeters (0.25-0.65 mm). Accordingly, the first rectangular rib 210a not only tapers slightly in radius, but also tapers in width when extending from a position near the attachment to the barrel 16' to an area proximate its attachment to the cap 204. The second rectangular rib 210b preferably has the same root width $W_R$ and head width $W_H$ as the first rectangular rib 210a, but is not so limited. The tapering of the first and second rectangular ribs 210a, 210b from their root width $W_R$ near the attachment to the barrel 1.6' to the head width $W_H$ proximate attachment to the cap 204 provides additional strength to the first and second rectangular ribs 210a, 210b at their roots proximate attachment to the barrel 16' and also limits material for constructing the rib section 202 proximate attachment to the cap 204. The first and second rectangular ribs 210a, 210b are not limited to tapering in their widths $W_R$, $W_H$ from root to head and may have a relatively constant root width $W_R$ compared to head width $W_H$ or may taper outwardly such that the head width $W_H$ is greater than the root width $W_R$, depending upon design considerations and applications for the particular syringe 14'. In addition, the root width $W_R$ compared to head width $W_H$ are not limited to having the above-described dimensions and may be adapted to have nearly any size depending on the desired configuration and requirements for the hub 200 for a particular application.

The first T-shaped rib 212a has a T-root width $W_{TR}$ and a T-head width $W_{TH}$. The T-root width $W_{TR}$ is greater than the T-head width $W_{TH}$ in the third preferred embodiment. In the third preferred embodiment, the rectangular root width $W_R$ is approximately five to nine tenths millimeters (0.5-0.9 mm) and the rectangular head width $W_H$ is approximately twenty-five to sixty-five hundredths millimeters (0.25-0.65 mm). Accordingly, the first T-shaped rib 212a not only tapers slightly in radius, but also tapers in width when extending from a position near the attachment to the barrel 16' to an area proximate its attachment to the cap 204. The second T-shaped rib 212b preferably has the same T-root width $W_{TR}$ and T-head width $W_{TH}$ as the first T-shaped rib 212a, but is not so limited. The tapering of the first and second I-shaped ribs 212a, 212b from their T-root width $W_{TR}$ near the attachment to the barrel 16' to the T-head width $W_{TH}$ proximate attachment to the cap 204 provides additional strength to the first and second rectangular ribs 210a, 210b at their roots proximate attachment to the barrel 16' and also limits material for constructing the rib section 202 proximate attachment to the cap 204. The first and second T-shaped ribs 212a, 212b are not limited to tapering in their widths $W_{TR}$ $W_{TH}$ from root to head and may have a relatively constant T-root width $W_{TR}$ compared to T-head width $W_{TH}$ or may taper outwardly such that the T-head width $W_{TH}$ is greater than the T-root width $W_{TR}$, depending upon design considerations and applications for the particular syringe 14'. In addition, the T-root width $W_{TR}$ and T-head width $W_{TH}$ are not limited to having the above-described dimensions and may be adapted to have nearly any size depending on the desired configuration and requirements for the hub 200 for a particular application.

In the third preferred embodiment, the first pair of ribs 210 have a generally rectangular cross-section and the second pair of ribs 212 have a generally H-shaped cross-section. The areas between the first and second pairs of ribs 210, 212 form or define the longitudinal voids 201 of the rib section 202. In addition, the first and second pairs of ribs 210, 212 define the cruciform-shape of the cross-section of the rib section 202 of the third preferred embodiment.

Figure 16A:
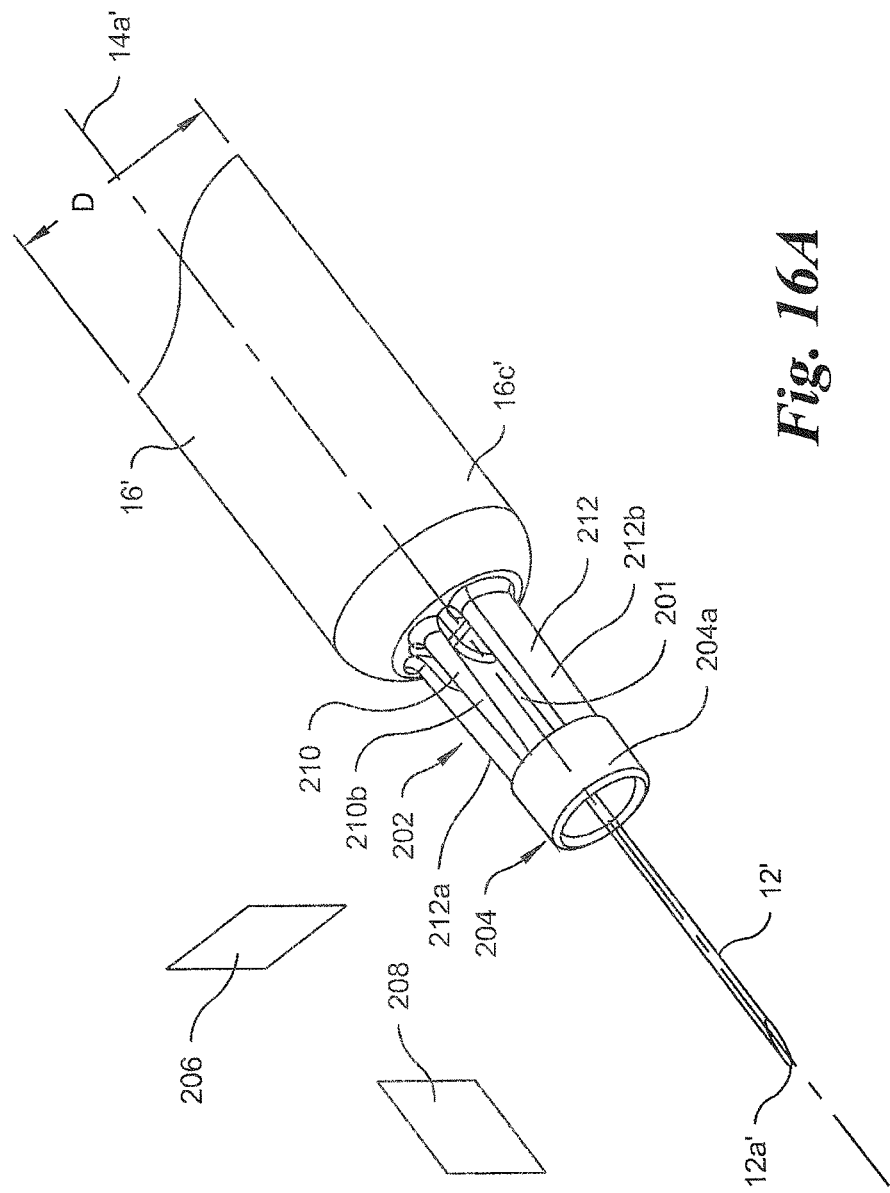
FIG. 16A is a magnified front perspective view of a distal end portion of the syringe of FIG. 14, taken from within dashed circle 16 of FIG. 14.

Referring to FIGS. 14-16, the hub 200 also includes the cap 204 which has a generally U-shaped crossed-section taken along a longitudinal plane 208. The longitudinal plane 208 is generally parallel to the longitudinal axis 14a'. The cap 204 is not limited to having the U-shaped cross-section including the upstanding wall 204a and the base 204b of the third preferred embodiment and may have nearly any size and/or shape that is able to engage with the needle shield 25 and withstand the normal operating conditions of the needle 14'. For example, the cap 204 may have a generally solid or puck-shaped configuration that engages the cannula 12' along the longitudinal axis 14a'. However, the U-shaped cross-section of the third preferred embodiment of the cap 204 limits material required for forming the cap 204 and the hub 200, similar to the above-described rib section 202.

Referring to FIGS. 14-18, the barrel 16', rib section 202 and cap 204 are all preferably constructed of a polymeric material and are co-molded with the cannula 12' utilizing the above-described molding method. The cannula 12' is preferably fixed to the syringe 14' during the co-molding process at its proximal end 12b' in the rib section 202. Specifically, the co-molded polymeric material preferably flows into and fixably engages the notches 18' at the proximal end 12b' of the cannula 12' during the co-molding process. The cannula 12' is not limited to being fixedly secured to the hub 202 by the co-molding process and engagement with the rib section 202 and may be co-molded for engagement at the cap 204, the distal end 16c', adhesively bonded to the hub 200 or otherwise fixedly secured to the barrel 16'.

Referring to FIGS. 17 and 18, in the third preferred embodiment, the first and second T-shaped ribs 212a, 212b include bulbous distal ends and relatively narrowed stems proximate the longitudinal axis 14a'. The T-root width $W_{TR}$ and T-head width $W_{TH}$ of the first and second T-shaped ribs 212a, 212b are taken at the bulbous distal ends of the first and second T-shaped ribs 212a, 212b. The T-shaped ribs 212a, 212b provide additional strength and stiffness for the first and second T-shaped ribs 212a, 212b and the hub 200, particularly under bending loads. The first and second T-shaped ribs 212a, 212b of the third preferred embodiment are not limiting and the second pair of ribs 212 may have a generally rectangular shape, circular shape, arcuate shape or nearly any shape that provides strength and stiffness to the rib section 202 and is able to withstand the normal operating conditions of the prefilled syringe 14'.

Referring to FIGS. 1A and 15, the needle shield 25 preferably includes a relatively hard, rigid shell 25a and a relatively soft plug 25b fixed or secured inside the rigid shell 25a. In the preferred mounted position, the soft plug 25b engages the cap 204 and the tip 12a' is embedded in the material of the soft plug 25b. Accordingly, the soft plug 25b limits leakage of medicament from the syringe 14' when the needle shield 25 is mounted to the cap 204. In addition, even if the tip 12a' is not embedded in the soft plug 25b, the needle shield 25 and cap 204 generally limit leakage of the medicament from outside the bounds of the needle shield 25 and cap 204.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

Further, to the extent that the method does not rely on the particular order of steps set forth herein, the particular order of the steps in the steps set forth in the preferred method should not be construed as a limitation. One skilled in the art can readily appreciate that the steps may be varied and still remain within the spirit and scope of the present invention.

I claim:

1. A prefilled syringe for injecting medicament into a patient, the syringe comprising:
    a barrel constructed of a polymeric material, the barrel including a diameter, a longitudinal axis, a proximal end and a distal end;
    a cannula having a proximal end and a tip opposite the proximal end, the proximal end of the cannula fixed to the distal end of the barrel, the cannula positioned generally coaxially with the longitudinal axis; and
    a hub integrally formed with the distal end, the hub including a rib section and a cap, the rib section including a first pair of ribs and a second pair of ribs, the first pair of ribs having a generally rectangular-shaped cross-section and the second pair of ribs having a generally H-shaped cross-section, the cannula co-molded with the rib section.

2. The prefilled syringe of claim 1 wherein the rib section has a generally cruciform cross-section taken along a rib plane, the rib plane being generally perpendicular to the longitudinal axis.

3. The prefilled syringe of claim 1 wherein the cap has a generally U-shaped cross-section taken along a longitudinal plane, the longitudinal plane being generally parallel to the longitudinal axis.

4. The prefilled syringe of claim 1 wherein the first pair of ribs include a first rectangular rib and a second rectangular rib, the first rectangular rib having a first radius and the second rectangular rib have a second radius, the first radius being generally equal to the second radius.

5. The prefilled syringe of claim 1 wherein the second pair of ribs include a first T-shaped rib and a second T-shaped rib, the first T-shaped rib having a third radius and the second T-shaped rib having a fourth radius, the third radius being generally equal to the fourth radius.

6. The prefilled syringe of claim 1 further comprising:
a needle shield configured for removable mounting to the cap, the cap being tapered to allow the needle shield to removably mount to the syringe, the cap including an upstanding wall and a base, the upstanding wall engaging the needle shield in a mounted position, the engagement between the needle shield and the upstanding wall limiting leakage of the medicament in the mounted position.

7. The prefilled syringe of claim 6 wherein the cap is generally hollow, the cap having a U-shaped cross-section taken along a longitudinal plane that extends through and generally parallel with the longitudinal axis.

8. The prefilled syringe of claim 1 wherein the first pair of ribs includes a first rectangular rib and the second pair of ribs includes a first T-shaped rib, the first rectangular rib has a first radius and the first T-shaped rib has a third radius, the first radius being generally equal to the third radius.

9. The prefilled syringe of claim 1 wherein the cannula includes notches defined in the proximal end of the cannula, the hub in facing engagement with the cannula at the proximal end, the notches configured for affixing and securing the proximal end to the hub.

\* \* \* \* \*